(12) United States Patent
Nair et al.

(10) Patent No.: US 6,308,001 B1
(45) Date of Patent: Oct. 23, 2001

(54) RADIATION CURABLE FLUORINATED VINYL ETHERS DERIVED FROM HEXAFLUOROPROPENE

(75) Inventors: Haridasan K. Nair; David Nalewajek; David E. Bradley, all of Erie County, NY (US)

(73) Assignee: AlliedSignal Inc., Morris Township, NJ (US)

(*) Notice: Subject to any disclaimer, the term of this patent is extended or adjusted under 35 U.S.C. 154(b) by 0 days.

(21) Appl. No.: 09/218,201

(22) Filed: Dec. 22, 1998

(51) Int. Cl.[7] ........................................ G02B 6/00
(52) U.S. Cl. .............. 385/143; 385/145; 385/129; 522/25; 522/31; 522/32; 522/90; 528/32; 528/34; 528/37
(58) Field of Search ............... 522/25, 31, 99, 522/170, 181; 528/32–37; 385/143, 145, 129, 130

(56) References Cited

U.S. PATENT DOCUMENTS

| | | | |
|---|---|---|---|
| 2,732,370 | 1/1956 | Codding | 260/91.1 |
| 3,394,116 | 7/1968 | Sorkin . | |
| 3,504,016 | 3/1970 | Smeltz | 260/475 |
| 4,559,179 | 12/1985 | Hisamoto et al. | 260/456 |
| 5,012,011 | 4/1991 | Liu et al. | 568/610 |
| 5,024,507 | 6/1991 | Minns et al. . | |
| 5,054,872 | 10/1991 | Fan et al. | 385/130 |
| 5,274,174 | 12/1993 | Shah et al. | 560/130 |
| 5,511,142 | 4/1996 | Horie et al. | 385/129 |
| 5,562,858 | 10/1996 | Bartmann et al. | 252/299.66 |
| 5,624,762 * | 4/1997 | Glover et al. | 522/99 |
| 5,705,316 * | 1/1998 | Steinmann et al. | 522/170 |
| 5,824,761 * | 10/1998 | Bujanowski et al. | 528/25 |
| 6,028,124 * | 2/2000 | Glover et al. | 522/181 |

FOREIGN PATENT DOCUMENTS

| | | |
|---|---|---|
| 02000721 | 1/1990 | (JP) . |
| 2000721 | 1/1990 | (JP) . |
| WO 99/36381 | 7/1999 | (WO) . |

OTHER PUBLICATIONS

Kaino, "Polymer Optical Fibers," *Polymers for Lightwave and Integrated Optics*, (Hornak, Ed., Marcel Dekker, New York, 1992), 1–36.

Monroe et al., "Photopolymers for Holography and Waveguide Applications," *Polymers for Lightwave and Integrated Optics*, (Hornack Ed., Marcel Dekker, New York, 1992), 145–166.

Sukhinin et al., *Zh. Vses. khim. O–va*, 26(3), 344–5 (1981).

Ando et al., *Chemtech*, 20 (1994).

Cote et al., *Annu. Int. Conf. Text. Coat. Laminating, 6th*, paper 15, 1–9 (1996).

* cited by examiner

*Primary Examiner*—Phan T. H. Palmer
*Assistant Examiner*—Sang H. Nguyen
(74) *Attorney, Agent, or Firm*—Colleen D. Szuch

(57) ABSTRACT

Vinyl ether compounds having the formula:

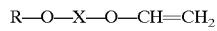

R—O—X—O—CH=CH$_2$ wherein R is a radical having the formula: R$_1$—CFH—CF$_2$— or R$_1$—CF=CF—, wherein R$_1$ is an unsubstituted or substituted aliphatic radical, unsubstituted or substituted cyclic aliphatic radical, an unsubstituted or substituted aromatic radical, an unsubstituted or substituted araliphatic radical, or an unsubstituted or substituted heterocyclic radical, and X is an unsubstituted or substituted aliphatic radical, an unsubstituted or substituted cyclic aliphatic radical, unsubstituted or substituted aromatic radical, unsubstituted or substituted araliphatic radical or an unsubstituted or substituted heterocyclic radical. Curable compositions containing the vinyl ether compounds and methods in which the substrate coating layers of the vinyl ether compositions are cured, particularly on optical devices, are also disclosed, as well as polymers polymerized from the vinyl ether compounds.

25 Claims, No Drawings

RADIATION CURABLE FLUORINATED VINYL ETHERS DERIVED FROM HEXAFLUOROPROPENE

FIELD OF INVENTION

The present invention relates to useful fluorinated compounds. More specifically, this invention relates to a family of fluorinated vinyl ether compounds, their uses, and the products resulting from their use.

BACKGROUND OF THE INVENTION

Vinyl ethers containing fluorine are of particular interest in coatings applications because they form polymers and copolymers that exhibit beneficial properties, including high chemical and thermal resistance, high electrical resistivity, low surface energy and low refractive index. These properties can be imparted to a coating surface and, consequently, fluorinated vinyl ethers are particularly useful in making protective release coatings, as well as, surfactants, anticorrosion agents, antioxidizing agents and the like.

Moreover, vinyl ether monomers or copolymers that can be cured via ultraviolet (UV) radiation offer even more advantages in coatings and other applications. Photocuring technology has grown rapidly within the last decade. The photocuring process involves the radiation induced polymerization or cross linking of monomers into a three dimensional network and has a number of advantages including the environmentally safe, solvent-free 100% conversion to a desired product, as well as short cycle times and limited space and capital equipment requirements.

In the telecommunications industry, for example, there is a need to develop photocurable compositions for optical wave guide and interconnect applications. In order to be useful in these applications, the photocurable compositions must polymerize to form polymers that are highly transparent at the working wavelength and possess low intrinsic absorption and scattering loss.

Unfortunately, in the near-infrared region, between 1330 and 1550 nm, many polymers formed from photocurable materials possess neither the required transparency nor low intrinsic absorption loss. There remains a need for new monomers that polymerize to form infrared-transparent polymers with low intrinsic absorption loss.

DETAILED DESCRIPTION OF THE INVENTION

The present invention provides a family of fluorinated vinyl ether compounds which are useful for making other compounds, including polymeric compounds, having a wide variety of uses. The vinyl ether compounds of the present invention exhibit the beneficial properties of fluorinated monomers and can be utilized to realize the benefits of photocuring processes.

According to the present invention fluorinated vinyl ether compounds are provided having the structure of Formula I:

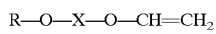

wherein R is a radical having the formula: $R_1$—CFH—$CF_2$— or $R_1$—CF=CF—, wherein $R_1$ is an unsubstituted or substituted aliphatic radical, an unsubstituted or substituted cyclic aliphatic radical, an unsubstituted or substituted aromatic radical, an unsubstituted or substituted araliphatic radical, or an unsubstituted or substituted heterocyclic radical; an X is an unsubstituted or substituted aliphatic radical, an unsubsituted or substituted cyclic aliphatic radical, an unsubstituted or substituted aromatic radical, an unsubstituted or substituted araliphatic radical, or an unsubstituted or substituted heterocyclic radical.

According to one aspect of the present invention, monomer compounds are provided having the structure of Formula I, provided, however, that when X is a substituted biphenyl radical, $R_1$ is not a trifluoromethyl group.

Another aspect of the present invention provides curable compositions that contain a curable component that includes at least one compound having the structure of Formula I, in which R and X are as described above for Formula I, and an initiator compound or a catalyst compound for the curable component. Preferred curable compositions include photocurable compositions combining at least one compound having the structure of Formula I and a photoinitiator compound. The curable component of the curable compositions of the present invention includes compounds of Formula I in which $R_1$ of R is a trifluoromethyl group when X is a substituted biphenyl radical.

The curable compositions of the present invention are useful in the manufacture of optical devices having light transmissive regions. Therefore, another aspect of the present invention provides a process for producing an optical device employing the steps of: (a) applying a layer of the photocurable composition of the invention onto a substrate; (b) imagewise exposing the photocurable composition of the invention to actinic radiation to form exposed and non-exposed areas on the substrate; and (c) removing the imagewise non-exposed areas while leaving the imagewise exposed areas on the substrate.

Yet another aspect of the invention comprises the light transmissive component of a waveguide produced in the above-identified process.

In the process of the present invention in which an optical device is produced, the fluorinated vinyl ether compounds of the present invention are cured by polymerization to form a polymeric coating on a substrate. The present invention therefore also includes the polymers produced by curing the fluorinated vinyl ether compounds of the present invention. Therefore, a further aspect of the invention provides a polymer with one or more vinyl ether repeating units having the structure of Formula II:

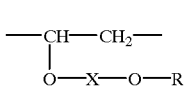

(II)

wherein R and X are as described above with respect to Formula I. The polymers of the present invention include polymers having vinyl ether repeating units in which $R_1$ of R is a trifluoromethyl group when X is a substituted biphenyl radical.

In Formulae I and II, X is preferably an unsubstituted or substituted $C_1$–$C_{20}$ aliphatic radical, an unsubstituted or substituted $C_3$–$C_{20}$ cyclic aliphatic radical, an unsubstituted or substituted $C_6$–$C_{15}$ aromatic radical, an unsubstituted or substituted $C_7$–$C_{13}$ araliphatic radical, or an unsubstituted or substituted 3–10 member heterocyclic radical. More preferably, X is an unsubstituted or substituted $C_1$–$C_{20}$ alkyl radical, an unsubstituted or substituted $C_3$–$C_{10}$ cycloalkyl radical, an unsubstituted or substituted 3–6 member heterocyclic radical, an unsubstituted or substituted $C_6$–$C_{15}$ aryl radical, or an unsubstituted or substituted $C_7$–$C_{13}$ aralkyl radical. The radicals may be substituted with essentially any conventional organic moiety. Examples of substitution groups include $C_1$–$C_6$ aliphatics such as alkyls, halogenated alkyls, alkoxys, and alkenyls, $C_6$–$C_{15}$ aryls, halogens, particularly fluorine, $C_3$–$C_8$ cyclic aliphatics, nitros, aminos (primary and secondary), amidos, cyanos and hydroxyls.

X as a $C_1$–$C_{20}$ alkyl radical may be straight chain or branched, for example, a methyl, ethyl, n-propyl, isopropyl, n-butyl, isobutyl, tert-butyl, n-pentyl, neopentyl, n-hexyl, n-heptyl, n-octyl, or 2-ethylhexyl radical. Any of these groups may be substituted with typical organic moieties, such as methoxy, ethoxy, n-propoxy, isopropoxy, n-butoxy, methanesulphonyl, cyano, bromine, chlorine or fluorine to form, for example, methoxymethyl, 2-methoxyethyl, 2-ethoxymethyl, 2-n-butoxyethyl, 3-methoxypropyl, 1-methoxybutyl, 2-methoxybutyl, methanesulphonylmethyl, 2-methanesulphonylethyl, 2-cyanoethyl, 2-fluoroethyl, 2,2,2-trifluoroethyl, trichloromethyl, 2-chloroethyl, 2-(chloromethyl)ethyl, 2,2,2-trichloroethyl, 2-chloro-n-propyl or 3-chloro-n-butyl. In a preferred class of alkyl radicals, X is a straight chain $C_2$–$C_6$ alkyl radical, especially an ethyl or butyl radical.

X as a $C_3$–$C_{10}$ cycloalkyl radical may be, for example, a cyclopropyl, cyclobutyl, cyclopentyl, methylcyclopentyl, cyclohexyl, methylcyclohexyl dimethylcyclohexyl, cycloheptyl, or cyclooctyl radical. Any of these groups may be substituted with essentially any conventional organic radical, including, for example, methoxy, ethoxy, n-propoxy, isopropoxy, n-butoxy, cyano, chlorine or fluorine. In a preferred class of cycloalkyl radical, X is a $C_6$–$C_{10}$ cycloalkyl radical. In a preferred class of cycloalkyl radical, X is a $C_6$–$C_8$ cycloalkyl radical, even more preferably, a cyclohexyldimethyl radical.

X as a 3–6 ring member heterocyclic radical may include known heterocyclic atoms such as N, O and S. Suitable heterocycles include, for example, pyran, thiophene, pyrrole, furan, pyridine, or derivatives thereof.

X as a $C_6$–$C_{15}$ aryl may be, for example, phenyl, o-tolyl, m-tolyl, p-tolyl, o-xylyl, m-xylyl, p-xylyl, alpha-naphthyl or beta naphthyl. Any of these groups may be substituted with essentially any conventional organic radical, for example, halogens, particularly fluorine, $C_1$–$C_4$ alkoxyl or nitro. In a preferred class of compounds, X is $C_6$–$C_{12}$ aryl, especially phenyl or naphthyl.

X as a $C_7$–$C_{20}$ aralkyl radical may be, for example, benzyl, 4-methylbenzyl, o-methylbenzyl, p-methylbenzyl, diphenylmethyl, 2-phenylethyl, 2-phenylpropyl or 3-phenylpropyl, preferably $C_7$–$C_9$ aralkyl, especially benzyl. In a still more preferred embodiment, X is an alkyl or aralkyl radical, especially a ethyl, butyl, or cyclohexyldimethyl radical.

For R of Formulae I and II, $R_1$ is preferably an unsubstituted or substituted $C_1$–$C_{12}$ aliphatic radical, an unsubstituted or substituted $C_3$–$C_{20}$ cyclic aliphatic radical, an unsubstituted or substituted $C_6$–$C_{15}$ aromatic radical, an unsubstituted or substituted $C_7$–$C_{13}$ araliphatic radical, or an unsubstituted or substituted 3–10 member heterocyclic radical. More preferably, $R_1$ is an unsubstituted or substituted $C_1$–$C_{12}$ alkyl radical, an unsubstituted or substituted $C_3$–$C_{10}$ cycloalkyl radical, an unsubstituted or substituted 3–6 member heterocyclic radical, an unsubstituted or substituted $C_6$–$C_{15}$ aryl radical, or an unsubstituted or substituted $C_7$–$C_{20}$ aralkyl radical. Examples of substitution groups include $C_1$–$C_6$ aliphatics such as alkyls, alkoxys and alkenyls, $C_6$–$C_{15}$ aryls, halogens, particularly fluorine, $C_3$–$C_8$ cyclic aliphatics, nitros, aminos (primary and secondary), amidos, cyanos, and hydroxyls.

$R_1$ as a $C_1$–$C_{12}$ alkyl radical may be straight chained or branched, for example, a methyl, ethyl, n-propyl, isopropyl, n-butyl, isobutyl, tert-butyl, n-pentyl, neopentyl, n-hexyl, n-heptyl, n-octyl or 2-ethylhexyl. Any of these groups may be substituted with essentially any conventional organic moiety, for example, methoxy, ethoxy, n-propoxy, isopropoxy, n-butoxy, methanesulphonyl, cyano, bromine, chlorine or fluorine.

More preferably, $R_1$ is a $C_1$–$C_{12}$ fluorinated alkyl radical. $C_1$–$C_6$ fluorinated alkyl radicals are even more preferred. The present invention contemplates the use of $C_3$ or $C_4$ to $C_{12}$ fluorinated alkyl radicals. The fluorinated alkyl group of $R_1$ may be straight chained or branched, for example, fluoromethyl, difluoromethyl, trifluoromethyl, fluoroethyl, difluoroethyl, trifluoroethyl, pentafluoroethyl, perfluoropropyl, perfluorobutyl, perfluoropentyl, or perfluorohexyl. In the most preferred form, $R_1$ is a trifluoromethyl radical.

$R_1$ as a $C_3$–$C_{10}$ cycloalkyl radical may be, for example, cyclopropyl, cyclobutyl, cyclopentyl, methylcylcopentyl, cyclohexyl, methylcyclohexyl, dimethylcyclohexyl, cycloheptyl or cyclooctyl. Any of these groups may be substituted by essentially any conventional organic moiety, for example, methoxy, ethoxy, n-propoxy, n-butoxy, methanesulphonyl, cyano, bromine, chlorine or fluorine. Of the $R_1$ cycloalkyl radicals, fluorine-substituted radicals are preferred.

$R_1$ as a 3–10 ring member heterocyclic radical may include known heterocyclic atoms such as N, O and S. Suitable heterocycles include, for example, pyran, thiophene, pyrrole, furan, pyridine or derivatives thereof.

$R_1$ as a $C_6$–$C_{15}$ aryl may be, for example, phenyl, o-tolyl, m-tolyl, p-tolyl, o-xylyl, m-xylyl, p-xylyl, alpha-napthyl, or beta-napthyl. Any of these groups can be substituted with, essentially any conventional organic radical, for example, halogen, preferably fluorine, $C_1$–$C_4$ alkoxyl or nitro.

$R_1$ as a $C_7$–$C_{20}$ aralkyl radical may be, for example, benzyl, 4-methylbenzyl, o-methylbenzyl, p-methylbenzyl, diphenylmethyl, 2-phenylethyl, 2-phenylpropyl, or 3-phenylpropyl, preferably $C_7$–$C_9$ aralkyl, especially benzyl. Any of these groups may also be substituted with essentially any conventional organic moiety, for example, halogen, preferably fluorine, $C_1$–$C_4$ alkoxyl or nitro. The halogen, alkoxyl or nitro may be substituted in the aryl portion of the group, or in the alkyl portion of the group. Aryl and aralkyl $R_1$ groups are preferably fluorinated, and the fluorine may be substituted in either the aryl group or the aryl portion of the aralkyl group to form, for example, a mono-, di-, tetra-, tert- or penta-fluorophenyl group, or the fluorine may be substituted in the alkyl portion of the aralkyl group to form, for example, mono-, di- or tetra-fluorobenzyl.

The compounds of Formula I may exist in isomeric form. For example, when R is $R_1$—CFH—$CF_2$, the compounds of Formula I have an asymmetric carbon at the —CFH— position, and consequently, they can exist in the form of different combinations of R- and S-isomeric forms as enantiomers or racemates. In addition, cis and trans geometric isomers may also be present in the subject compounds. All racemic and isomeric forms of the compounds of Formula I, including pure enantiomeric, racemic and geometric isomers and mixtures thereof, are within the scope of the invention.

The compounds of the invention were prepared by the Reaction Scheme I, shown below:

Reaction Scheme I

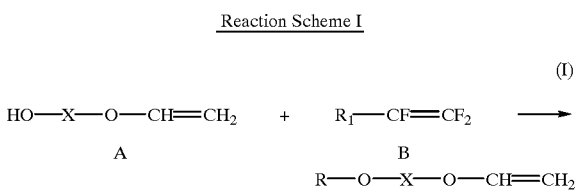

A variety vinyloxyalcohols are commercially available, including, for example, Compound A, wherein X is a ethyl or butyl radical (available from Aldrich Chemical Co.); or a cyclohexyldimethyl radical (available from BASF Corp.). Furthermore, many compounds having the structure of Compound A are known in the literature and are obtainable by art-recognized procedures, see, for example, Sukhinin, et al., *Zh.Vses. Khim.O-va.*, 26(3), 344–5 (1981).

The Compound B fluorinated olefins are also commercially available, including, for example, hexafluoropropene, perfluorohexene, and perfluoroheptene commercially available from Aldrich Chemical Co. Additionally, other Compound B fluorinated olefins are reported in the literature and are obtainable by procedures familiar to those skilled in the art.

A number of methods for the preparation of vinyl ethers are known, see Fischer, P. *Enol Ethers-Structure, Synthesis and Reactions,* p. 761–920, in Patai, S., Editor "Chemistry of Ethers, Crown Ethers, Hydroxyl Groups and Their Sulfur Analogues" (Wiley, Chichester, UK (1980). The conversion of Compound A to compounds of Formula I may be accomplished by slight modification of the procedures reported in Bayliff, et al., *J. Chem. Soc. Perkin Trans.* 1, 4, 763–767, (1987) and Kanunyants, et al., *Izv. Akad. Nauk SSSR Otdel. Khim. Nauk,* 282 (1953). The disclosures of these publications are incorporated herein by reference.

In a typical procedure, a mixture of Compound A, an aprotic solvent, and a base is stirred, with slow addition, preferably dropwise, of a Formula B fluorinated olefin. Preferably about 2.0 to 2.5 parts by weight of solvent per part by weight of Compound A is employed. However, those of ordinary skill in the art will understand how to successfully employ higher or lower quantities of solvent. Although the reaction is not inhibited by oxygen, it is preferred to conduct the reaction under a blanket of an inert gas such as, for example, nitrogen.

Suitable aprotic solvents include, for example, acetonitrile, dimethylformamide, and tetrahydrofuran. In a preferred embodiment, the aprotic solvent is acetonitrile.

The temperature at which the reaction mixture is stirred before and during addition of the fluorinated olefin and the strength of the base used in the aforementioned reaction are factors believed to determine whether the radical R in the product is an unsaturated radical of the formula $R_1$—CF=CF—, or whether the addition product $R_1$—CHF—$CF_2$— is formed.

When the reaction mixture is stirred at a low temperature, typically between about −40° C. and about 30° C., and preferably between about −10° C. to about 20° C., and a weak base is used, the addition product is formed. For purposes of the present invention, a "weak base" is defined as a base that is a weaker base than the carbon-carbon double bond of Compound B of Reaction Scheme I. Such bases are readily identified by those of ordinary skill in the art and include, but are not limited to, metallic carbonates, tertiary organic amines and alkoxides. Preferred carbonates include potassium carbonate and cesium carbonate, with potassium carbonate being more preferred. Preferred organic amines include triethylamine and pyridine.

A minor amount of unsaturated byproduct (R is $R_1$—CF=CF—) will remain in a cis/trans mixture. If desired, one skilled in the art can readily reduce this amount by routine optimization of the reaction conditions.

To prevent the formation of the addition product, higher temperatures, i.e., greater than 30° C. and up to about 80° C., and strong bases should be employed. Suitable strong bases include, for example, metallic hydroxides, metallic hydrides, metallic alkoxides, alkyl metallics, metallic oxides, and the like. Preferred metallic hydroxides include, for example, sodium hydroxide and potassium hydroxide. Preferred metallic hydrides include, for example, sodium hydride. In a preferred embodiment, the strong base is sodium hydroxide. Under the reaction conditions for preventing the formation of the addition product, very little, if any, of the addition product is formed. The amount that is formed can be reduced, or even eliminated, by routine optimization of reaction conditions.

The amount of base used in the synthesis of compounds of Formula I can range from catalytic to a stoichiometric amount. Catalytic amounts typically range between about 0.1 to about 20 mole percent relative to the hydroxyvinyl alcohol (Compound A) of Reaction Scheme I. In light of this disclosure, one skilled in the art can readily optimize the amount of base used in the reaction without undue experimentation.

The compounds of Formula I obtained from the aforementioned reaction may be purified by conventional methods known to those skilled in the art. For example, aqueous washes, drying, concentrating under reduced pressure, distillation, and the like may be used.

The compounds of the present invention will be useful in a number of applications, especially in such high technology areas as optical fibers, optical instruments and equipment, electronics, coatings, laminates, and extruded or molded shapes and articles, for example, for equipment exposed to a corrosive environment such as integrated circuit fabricating equipment. Coatings derived from compounds of the present invention may be applied for example, to capacitors, resistors, and integrated circuits, for the purpose of encapsulating them to protect them from harmful environment or to provide a highly dielectric layer; to plastic sheets or metal foils for the purpose of protecting them from damage or for making laminates; to interior walls of reactors, especially those employed in highly corrosive reaction with concentrated acids or with hydrofluoric acid, to protect them from corrosion; to light-transmissive devices such as optical lenses, prisms, and glazing to impart to them improved abrasion resistance or resistance against damage in corrosive environments; to glass or quartz cores for optical fibers to form a cladding; and recording heads, disks, and tapes, and to components of radio and microwave receiving equipment such as antenna dishes, etc. to protect them from mechanical or environmental damage.

The present invention also provides for a curable composition comprising at least one compound of Formula I. When only a compound of Formula I is present, the resulting polymer is a homopolymer. When other monomers are present, a copolymer is produced.

The compositions may be curable by application of heat energy or exposure to actinic radiation. Initiator compounds may be employed. Microwave radiation may be used to apply heat to the composition. The compositions may also be catalytically cured without application of heat or exposure to actinic radiation, for example, by using an effective amount of a Lewis Acid catalyst, such as $BF_3$.

For purposes of the present invention, compositions that are curable by exposure to actinic radiation are defined as being "photocurable." Suitable sources of actinic radiation include light in the visible, ultraviolet or infrared regions of the spectrum, as well electron beam, ion or neutron beam or X-ray radiation. Actinic radiation may be in the form of incoherent light or coherent light such as light from a laser.

Photocurable compositions according to the present invention preferably contain a photoinitiator compound. Suitable photoinitiator compounds may be readily selected by those skilled in the art, and include, for example, DAROCUR 1173, DAROCUR 4265, IRGACURE 184, IRGACURE 261, IRGACURE 369, IRGACURE 500, IRGACURE 651, IRGACURE 784, IRGACURE 907, IRGACURE 1700, IRGACURE 2959, IRGACURE 1800, IRGACURE 1850, IRGACURE 819, AND IRGACURE 1300 (each commercially available from Ciba Specialty Chemicals) and GE-PI (commercially available from GE Corporation). The initiator is present in an amount sufficient to effect polymerization of the curable component. The initiator may comprise from about 0.01 to about 10% by weight, preferably from about 0.1 to about 6% by weight, and more preferably from about 0.5 to about 4% by weight of the total curable composition. Photocurable compositions contain an amount of a photoinitiator within the foregoing ranges that is sufficient to effect photopolymerization of the photocurable component upon exposure to sufficient actinic radiation.

The amount of curable component in the curable compositions may vary widely. Typically, the component is present in an amount of from about 35 to about 99% by weight of the overall composition. In a preferred embodiment, the curable component is present in an amount of from about 80 to about 99% by weight, and, more preferably, from about 95 to about 99% by weight of the overall composition. Photocurable compositions contain an amount of the curable component within the foregoing ranges that is sufficient to photocure and provide image differentiation upon exposure to sufficient actinic radiation.

In addition to the compound of Formula I, other curable compounds which are known in the art may be incorporated into the curable compositions of the present invention. These compounds include monomers, oligomers and polymers containing at least one terminal ethylenically unsaturated group and being capable of forming a high molecular weight polymer by free radical initiated, chain propagating addition polymerization. Suitable monomers include, but are not limited to, ethers, esters and partial esters of: acrylic and methacrylic acids; aromatic and aliphatic polyols containing from about 2 to about 30 carbon atoms; and cycloaliphatics polyols containing from about 5 to about 6 ring carbon atoms. Specific examples of compounds within these classes are: ethylene glycol diacrylate and dimethacrylate, diethylene glycol diacrylate and dimethacrylate, triethylene glycol diacrylate and dimethacrylate, hexane diacrylate and dimethacrylate, trimethylolpropane triacrylate and trimethacrylate, dipentaerythritol pentaacrylate, pentaarcrylate, pentaerthrytol triacrylate, pentaerythrytol tetraacrylate and trimethacrylate, alkoxylated bisphenol-A diacrylates and dimethacrylates (e.g., ethoxylated bisphenol-A diacrylate and dimethacrylate and propoxylated bisphenol-A diacrylates and dimethacrylates), alkoxylated hexafluorobiphenol-A diacrylates and dimethacrylates and mixtures of the above compounds. Preferred monomers include multifunctional aryl acrylates and methacrylates. Preferred arylacrylate monomers include di-, tri- and tetra-acrylates and methacrylates based on the bis-phenol-A structure. More preferred arylacrylate monomers are alkoxylated bisphenol-A diacrylates and dimethacrylates such as ethoxylated bisphenol-A diacrylates and dimethacrylates, and ethoxylated hexafluorobisphenol-A diacrylates and dimethacrylates.

Suitable oligomers include, but are not limited to, epoxy acrylate oligomers, aliphatic and aromatic urethane acrylate oligomers, polyester acrylate oligomers, and acrylated acrylic oligomers. Epoxy acrylate oligomers (such as Ebercryl 600 by Radcure) are preferred.

Suitable polymers include, but are not limited to, acrylated polyvinyl alcohols, polyester acrylates and methacrylates, acrylated and methacrylated styrene-maleic acid co-polymers. Acrylated styrene-maleic acid copolymers are preferred.

When other ethylenically unsaturated monomers, oligomers or polymers are employed, the weight ratio of the monomer compound of Formula I to the ethylemically unsaturated compounds may vary from about 1:9 to about 9:1, and preferably from about 1:1 to about 9:1.

Various optional additives may also be added to the curable compositions of the invention depending upon the application in which they are to be used. Examples of these optional additives include antioxidants, photostabilizers, volume expanders, fillers (e.g., silica and glass spheres), dyes, free radical scavengers, contrast enhancers and UV absorbers.

Antioxidants include such compounds as phenols and particularly hindered phenols including Irganox 1010 from Ciba Specialty Chemicals; sulfides; organoboron compounds; organo-phosphorus compounds; and N,N'-hexamethylene-bis(3,5-di-tert-(butyl-4-hydroxyhydrocinnamamide)) available from Ciba Specialty Chemicals under the tradename Irganox 1098. Photostabilizers and more particularly hindered amine light stabilizers include, but are not limited to, poly[(6-hexamethylene)2,2,6,6-tetramethyl-4-piperidyl)imino)] available from Cytech Industries under the tradename Cyasorb UV3346. Volume expanding compounds include such materials as the spiral monomers known Bailey's monomer. Suitable dyes include methylene green and methylene blue. Suitable free radical scavengers include oxygen, hindered amine light stabilizers, hindered phenols, and 2,2,6,6-tetramethyl-1-piperidinyloxy free radical (TEMPO). Suitable contrast enhancers include other free radical scavengers. UV absorbers include benzotriazoles and hydroxybenzophenone.

The additives may be used in amounts, based on the total composition weight, of from about 0 to about 6%, and preferably from about 0.1% to about 1%. Preferably all components of the curable composition are an admixture with one another, and, preferably, in a substantially uniform admixture.

The photocurable compositions of the invention can be used in the formation of the light transmissive element of an optical device. Examples of such devices are planar optical slab waveguides, channel optical waveguides, ribbed waveguides, optical couplers, routers, combiners and splitters. The photocurable composition of the invention can also be used in the formation of negative working photoresists and other lithographic elements such as printing plates. In a preferred embodiment of the invention, the photocurable composition is used for producing a waveguide comprising a substrate containing a light transmissive element. Such waveguides are formed by applying a film of the photocurable composition of invention to the surface of a suitable substrate. The film may be formed by any method known in the art, such as spin coating, dip coating, slot coating, roller coating and evaporation.

The substrate may be any material on which it is desired to establish a waveguide including semiconductor materials such as silicon, silicon oxide and gallium arsenide. In the event the light transmissive region on the substrate is to be made from a photocurable material which has an index of refraction which is lower than that of the substrate, an intermediate buffer layer possessing an index of refraction which is lower than the substrate must be applied to the substrate before the photocurable composition is added. Otherwise, the light loss in the waveguide will be unacceptable. Suitable buffers are made from semiconductor oxides, lower refractive index polymers or spin on silicon dioxide glass materials.

Once a film of the photocurable composition is applied to the substrate, actinic radiation is directed onto the film in order to delineate the light transmissive region. That is, the position and dimensions of the light transmissive device are determined by the pattern of the actinic radiation upon the surface of the film on the substrate. The photopolymers of the invention are conventionally prepared by exposing the photocurable composition to sufficient actinic radiation. For purposes of this invention, "sufficient actinic radiation" means light energy of the required wavelength, intensity and duration to produce the desired degree of polymerization action in the photocurable composition.

Sources of actinic light, exposure procedures, times, wavelengths and intensities may vary widely depending upon the desired degree of polymerization, the index of refraction of the photopolymer, and other factors known to those of ordinary skill in the art. The selection and optimization of these factors are well known to those skilled in the art.

Preferably that the photochemical excitation be carried out with relatively short wavelengths (or high energy) radiation so that exposure to radiation normally encountered before processing (e.g., room lights) will not prematurely polymerize the polymerizable material. The energy necessary to polymerize the photocurable compositions of the invention generally ranges from about 5 mW/cm$^2$ to about 200 mW/cm$^2$ with typical exposure times ranging from 0.1 second to about 5 minutes.

After the photocurable composition has been polymerized to form a predetermined pattern on the surface of the substrate, the pattern is then developed to remove the non-image areas. Any conventional development method can be used such as flushing the non-irradiated composition with a solvent. Suitable solvents include polar solvents, such as alcohols and ketones. The most preferred solvents are acetone, methanol, tetrahydrofuran and ethyl acetate.

While the preferred embodiment of the invention involves photocuring the photocurable composition, as noted above, one skilled in the art will appreciate that many variations of the method within the scope of the claims are possible depending upon the nature of the curable composition. For example, the composition may be heat-cured in an oven or through another heat source such as microwave radiation. Alternately, the composition may be cured using a Lewis Acid catalyst. Depending upon the particular use, the photocurable composition may be partially cured before application to a surface and subsequently fully cured.

The present invention also provides for a polymer comprising one or more vinyl ether repeating units, alone or with other repeating units, wherein the vinyl ether repeating units have the formula:

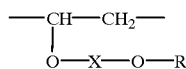

wherein X and R are the same as described above with respect to Formula I.

The vinyl ether repeating units are formed from the polymerization of compounds of Formula I, wherein R is a radical having the formula: $R_1$—CFH—CF$_2$ or $R_1$—CF=CF—.

In one embodiment, the polymer of the present invention may comprise only vinyl ether repeating units. The polymer may be a homopolymer, comprising first repeating units all derived from the same compound of Formula I, or the polymer may comprise two or more vinyl ether repeating units derived from different compounds of the present invention.

In an alternative embodiment, the polymer of the present invention may include one or more second repeating units derived from other monomers, oligomers, or polymer compounds that have been copolymerized with a vinyl ether compound of the present invention, and which are disclosed above as additional curable compounds that may be included in the curable compositions of the present invention.

EXAMPLES

In order that the invention may be more readily understood, reference is made to the following examples which are intended to be illustrative of the invention, but are not intended to be limiting in scope.

Example 1

Preparation of 1,1,1,2,3,3-hexafluoro-1-(2-vinyloxy ethyoxy)propane (CH$_2$=CH—O—CH$_2$CH$_2$—O—CF$_2$CFHCF$_3$) (1)

To a mechanically stirred mixture of ethyleneglycol vinyl ether (400 g, 4.54 mol), acetonitrile (800 mL), and potassium carbonate (K$_2$CO$_3$) (314 g, 2.27 mol, at 0° C. under nitrogen gas, was added hexafluoropropene (681 g, 4.54 mol) dropwise over a period of approximately 3 hours. The reaction flask was placed in an ice bath to moderate the exothermic reaction during the addition of hexafluoropropene. After complete addition of hexafluoropropene, the reaction mixture was stirred for an additional hour at room temperature and filtered. The filtrate was poured into 1.5 L water and mixed well. The lower organic layer formed was separated, washed with water (3×300 mL), and concentrated under reduced pressure (approximately 1 mm Hg). Distillation of this material at 30° C./3.2 mm Hg afforded 1,1,1,2,3,3-hexafluoro-1-(2-vinyloxy ethyoxy)propane as a colorless liquid (768 g, 71% yield); b.p. 30° C./3.2 mm Hg; Refractive Index 1.346 at 23.7° C.; GC/MS: m/z at 238 for M$^+$; $^{19}$F and $^1$H NMR spectral data are consistent with the structure.

Example 2

Preparation of 1,1,1,2,3,3-hexafluoro-1-(4-vinyloxy butoxy) propane (CH$_2$=CH—O—CH$_2$CH$_2$CH$_2$CH$_2$—O—CF$_2$CFHCF$_3$) (2)

To a mechanically stirred mixture of 1,4-butanediol vinyl ether (300 g, 2.57 mol), acetonitrile (600 mL), and K$_2$CO$_3$ (178 g, 1.29 mol), at 0° C. under nitrogen gas, was added hexafluoropropene (405 g, 4.54 mol) dropwise over a period of approximately 3 hours. The reaction flask was placed in an ice bath to moderate the exothermic reaction during the addition of hexafluoropropene. After complete addition of hexafluoropropene, the reaction mixture was stirred for an additional hour at room temperature and filtered. The filtrate was poured into 1.5 L water and mixed well. The lower layer formed was separated, washed with water (3×300 mL), and concentrated under reduced pressure (approximately 5 mm Hg), and distilled at 32–34° C./1 mm Hg to afford 1,1,1,2,3,3-hexafluoro-1-(4-vinyloxy butoxy)propane as a colorless liquid (580 g, 84% yield); b.p. 32° C./1.0 mm Hg; Refractive Index 1.373 at 23.7° C.; GC/MS: m/z at 266 for M$^+$; $^{19}$F and $^1$H NMR spectral data are consistent with the structure.

Example 3

Preparation of 1,1,2,3,3,3-hexafluoro-1-{[4-(vinyloxyethyl) cyclohexyl]methoxy}propane

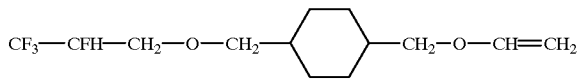

Hexafluoropropene (264 g, 1.76 mol) was added dropwise to a mechanically stirred mixture of 1,4-cyclohexanedimethanol vinyl ether (300 g, 1.76 mol), acetonitrile (600 mL), and K$_2$CO$_3$ (121 g, 0.88 mol), at 0° C. under N$_2$. The reaction flask was placed in an ice bath to moderate the exothermic reaction during the addition of hexafluoropropene. After complete addition of hexafluoropropene, the reaction mixture was stirred for an additional hour at room temperature and filtered. The filtrate was added to 1.5 L water and mixed well. The lower layer formed was separated, washed with water (3×300 mL), and concentrated under reduced pressure (approximately 0.05 mm Hg) to afford 1,1,2,3,3,3-hexafluoro-1-{[4(vinyloxymethyl)cyclohexyl]methoxy}propane(cis/trans mixture) as a colorless liquid (428 g, 76% yield); b.p. 55–60° C./0.05 mm Hg; Refractive Index 1.4145 at 23.7° C.; GC/MS: m/z at 320 for M$^+$; $^{19}$F and $^1$H NMR spectral data are consistent with the structure.

Example 4

Preparation of CF$_3$CF=CF—O—(CH$_2$)$_4$OCH=CH$_2$ (4)

To a mixture of CH$_2$=CH—O—(CH$_2$)$_4$—OH (100 g, 0.86 mol) and powdered sodium hydroxide (34.4 g., 0.86 mol.) under nitrogen was added hexafluoropropene (129 g, 0.86 mol) dropwise over a period of 1 hour at room temperature. The reaction flask was cooled by an ice-water bath to moderate the exothermic reaction. After complete addition of hexafluoropropene, the reaction mixture was stirred for another hour and poured into 500 mL of water. The lower layer was separated, concentrated on a rotary evaporator and distilled at 35–36/0.25 mmHg to afford 81 g of a colorless liquid which contained the products CF$_3$CF=CF—O—(CH$_2$)$_4$OCH=CH$_2$ and CF$_3$CFHCF$_2$—O—(CH$_2$)$_4$OCH=CH$_2$ in a 1:2 ratio. GC/MS for CF$_3$CF=CF—O—(CH$_2$)$_4$OCH=CH$_2$: m/z at 246 for M$^+$; $^{19}$F and $^1$H NMR spectral data are consistent with the structure.

Example 5

Preparation of CF$_3$CF=CF—O—(CH$_2$)$_2$OCH=CH$_2$ (5)

To a mixture of CH$_2$=CH—O—(CH$_2$)$_2$—OH (100 g, 0.86 mol) and powdered sodium hydroxide (35 g, 0.87 mol.) under nitrogen was added hexafluoropropene (129 g, 0.86 mol) dropwise over a period of 1 hour at room temperature. The reaction flask was cooled by an ice-water bath to moderate the exothermic reaction. After complete addition of hexafluoropropene, the reaction mixture was stirred for another hour and poured into 500 mL of water. The lower layer was separated, concentrated on a rotary evaporator and distilled at 35–36/3 mmHg and distilled at 35–36° C. to yield 76 g of 5 (30% yield).

Example 6

Preparation of the unsaturated product (6) of a hexafluoropropene trimer and CH$_2$=CH—O—(CH$_2$)$_2$—OH.

A mixture of hexafluoropropene trimer (20.25 g, 45 mmol), CH$_2$=CH—O—(CH$_2$)$_2$—OH (4.0 g, 45 mmol), cesium carbonate (325 mg), and acetonitrile was stirred at 50° C. for 14 hours. The reaction mixture was subsequently cooled to ambient temperature, and the lower layer was separated and washed with water. Additionally, more volatile materials were removed at 0.05 mmHg to afford a colorless viscous liquid (19% yield). GC/MS indicated a molecular ion at m/e 518 (C$_{13}$H$_7$F$_{17}$O$_2$) consistent with the unsaturated product (C$_9$F$_{17}$—OCH$_2$CH$_2$OCH=CH$_2$)

Example 7

Reaction of hexafluoropropene trimer with 1,4-butanediol vinylether

To a stirred mixture of 1,4-butanediol vinyl ether (116 g, 1.0 mol.), sodium t-butoxide (2 g, 0.02 mol.), cesium fluoride (1 g, 6 mmol.) and THF (200 mL) was gradually added hexafluoropropene trimer (100 g, 0.22 mol.). After this the reaction mixture was heated to ~70° C. and maintained at this temperature ~8 hours. Then the reaction mixture was cooled to room temperature, the lower layer was separated, washed with water, and more volatile materials were removed at 0.05 mm Hg to afford C$_9$F$_{18}$H—O—(CH$_2$)$_4$OCH=CH$_2$ as a colorless viscous liquid (yield=26%).

By following the procedure above, hexafluoropropene trimer adducts of ethyleneglycol vinyl ether and 1,4-cyclohexanedimethanol vinyl ether were obtained by substituting an equivalent amount of ethyleneglycol vinyl ether or 1,4-cyclohexanedimethanol, respectively, for the 1,4-butanediol vinyl ether used.

Example 8

Eight different cured polymeric films, A through H, were prepared in accordance with the present invention and the appearance and surface tension of each was recorded in Table I.

TABLE I

| Formulation Compound | Percent Compound in Composition | Appearance of liquid formulation | Appearance of cured film | Surface tension of liquid formulation (dyne/cm) | Surface tension of cured film (dyne/cm) |
|---|---|---|---|---|---|
| A. Compound 1 | 1.0 | cloudy | clear, smooth | 39 | 35 |
| B. Compound 1 | 10.0 | cloudy | clear, smooth | 39 | 31 |

TABLE I-continued

| Formulation Compound | Percent Compound in Composition | Appearance of liquid formulation | Appearance of cured film | Surface tension of liquid formulation (dyne/cm) | Surface tension of cured film (dyne/cm) |
|---|---|---|---|---|---|
| C. Compound 2 | 1.0 | clear | clear, smooth | 41 | 41 |
| D. Compound 2 | 5.0 | clear | clear, smooth | 41 | 41 |
| E. Compound 2 | 10.0 | clear | clear, smooth | 39 | 40 |
| F. Compound 3 | 1.0 | clear | clear, smooth | 48 | 42 |
| G. Compound 3 | 5.0 | clear | ND | ND | 42 |
| H. Compound 3 | 10.0 | clear | clear, smooth | ND | 40 |

Films A through H were prepared, in each case, by curing a photocurable composition comprised of: (1) an acrylate formulation comprised of: 80% by weight of Ebecryl 8804; 20% by weight of hexanediol diacrylate (HDODA); and 2 parts per hundred (pph) of Irgacure-651 (I-651); and (2) a compound of the present invention, specifically, either 1,1,1,2,3,3-hexafluoro-1-(2-vinyloxy ethyoxy)propane (Compound 1), 1,1,1,2,3,3-hexafluoro-1-(4-vinyloxy butoxy)propane (Compound 2), or 1,1,2,3,3,3-hexafluoro-1-{[4-(vinyloxymethyl)cyclohexyl]methoxy}propane (Compound 3). The compound of the invention used to make each film, and the percent by weight of the entire photocurable composition for each compound used in the formulations of films A through H is indicated in Table I.

Films A through H were prepared by curing the photocurable compounds under nitrogen using about 200–400 millijoules/cm$^2$ UV exposure from a mercury lamp. The surface tension of films A through H were measured as described in E. V. Sitzman et al., *Radtech 98 Proc.*, 72–82 (1998).

The foregoing table illustrates the enhanced surface properties of polymers prepared from the monomer compounds of the present invention. Films of the polymers were clear with the low surface energies (i.e., surface tension) required by many end-use applications.

What is claimed is:

1. A vinyl ether compound having the formula:

R—O—X—O—CH=CH$_2$ wherein R is a radical having the formula: R$_1$—CFH—CF$_2$— or R$_1$—CF=CF—, wherein R$_1$ is selected from the group consisting of unsubstituted and substituted aliphatic radicals, unsubstituted and substituted cyclic aliphatic radicals, unsubstituted and substituted aromatic radicals, unsubstituted and substituted araliphatic radicals and unsubstituted and substituted heterocyclic radicals; and X is selected from the group consisting of unsubstituted and substituted aliphatic radicals, unsubstituted and substituted cyclic aliphatic radicals, unsubstituted and substituted aromatic radicals, unsubstituted and substituted araliphatic radicals, and unsubstituted and substituted heterocyclic radicals;

provided that when X is a substituted biphenyl radical, R$_1$ is not a trifluoromethyl radical.

2. The compound of claim 1, wherein R$_1$ is a C$_1$–C$_{12}$ fluorinated aliphatic radical; and X is an alkyl or aralkyl radical.

3. The compound of claim 2, wherein X is a alkyl radical having the formula (—CH$_2$—)$_n$, wherein n is between 2 and 4, inclusive.

4. The compound of claim 3, wherein R$_1$ is a trifluoromethyl group.

5. The compound of claim 2, wherein said cyclic aliphatic group is a 1,4-cyclohexyldimethyl group.

6. The compound of claim 5, wherein R$_1$ is a trifluoromethyl group.

7. The compound of claim 2, wherein R$_1$ is a C$_3$–C$_{12}$ fluorinated aliphatic radical.

8. A curable composition comprising a curable component comprising at least one compound having the formula:

R—O—X—O—CH=CH$_2$ wherein R is a radical having the formula: R$_1$—CFH—CF$_2$— or R$_1$—CF=CF—, wherein R$_1$ is selected from the group consisting of unsubstituted and substituted aliphatic radicals, unsubstituted and substituted cyclic aliphatic radicals, unsubstituted and substituted aromatic radicals, unsubstituted and substituted araliphatic radicals and unsubstituted and substituted heterocyclic radicals; and X is selected from the group consisting of unsubstituted and substituted aliphatic radicals, unsubstituted and substituted cyclic aliphatic radicals, unsubstituted and substituted aromatic radicals, unsubstituted and substituted araliphatic radicals and unsubstituted and substituted heterocyclic radicals.

9. The composition of claim 8, wherein X is a alkyl radical having the formula (—CH$_2$—)$_n$, wherein n is between 2 and 4, inclusive.

10. The composition of claim 9, wherein R$_1$ is a trifluoromethyl group.

11. The composition of claim 8, wherein X is a 1,4-cyclohexyldimethyl group.

12. The composition of claim 11, wherein R$_1$ is a trifluoromethyl group.

13. The composition of claim 8, further comprising at least one ethylenically unsaturated monomer, oligomer, or polymer compound.

14. The composition of claim 8, wherein said curable component is present in an amount from about 35% to about 99.9% by weight of said composition.

15. The composition of claim 8, further comprising one or more additives selected from the group consisting of antioxidants, photostabilizers, volume expanders, fillers, dyes, free radical scavengers, contrast enhancers and UV absorbers.

16. The composition of claim 8, further including an initiator compound.

17. The composition of claim 16, wherein said initiator compound is a photoinitiator compound so that said composition is photocurable.

18. The composition of claim 16, wherein said initiator component is present in an amount from about 0.01 to about 10% by weight of the composition.

19. A polymer comprising one or more vinyl ether units having the formula:

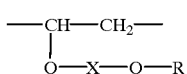

wherein R is a radical having the formula R$_1$—CFH—CF$_2$— or R$_1$—CF=CF—, wherein R$_1$ is selected from the group consisting of unsubstituted and substituted aliphatic radicals, unsubstituted and substituted cyclic aliphatic radicals, unsubstituted and substituted aromatic radicals, unsubstituted and substituted araliphatic radicals and unsubstituted and substituted heterocyclic radicals; and X is selected from the group consisting of unsubstituted and substituted aliphatic radicals, unsubstituted and substituted cyclic aliphatic radicals, unsubstituted and substituted aromatic radicals, unsubstituted and substituted araliphatic radicals and unsubstituted and substituted heterocyclic radicals.

20. The polymer of claim 19, wherein X is an alkyl group having the structure ($-CH_2-$)$_n$, wherein n is between 2 and 4, inclusive.

21. The polymer of claim 20, wherein $R_1$ is a trifluoromethyl group.

22. The polymer of claim 19, wherein X is a 1,4-cyclohexyldimethyl group.

23. The polymer of claim 22, wherein $R_1$ is a trifluoromethyl group.

24. The polymer of claim 19, wherein said polymer further comprises one or more second repeating units selected from the group consisting of monomers, olimers and polymers containing at least one terminal ethylenically unsaturated group and being capable of forming a high molecular weight polymer by free radical initiated chain propagating addition polymerization.

25. The polymer of claim 19 consisting essentially of said vinyl ether repeating units.

* * * * *